United States Patent [19]

Hughes et al.

[11] 4,432,370
[45] Feb. 21, 1984

[54] METHOD AND MEANS FOR MINIMALLY INVASIVE ANGIOGRAPHY USING MONO-CHROMATIZED SYNCHROTRON RADIATION

[75] Inventors: E. Barrie Hughes, Redwood City; Edward Rubenstein, Hillsborough; Robert Hofstadter, Stanford, all of Calif.

[73] Assignee: The Board of Trustees of the Leland Stanford Junior University, Palo Alto, Calif.

[21] Appl. No.: 311,305

[22] Filed: Oct. 14, 1981

[51] Int. Cl.³ .............................................. A61B 6/00
[52] U.S. Cl. ................................................... 128/654
[58] Field of Search ....................... 128/653, 654, 695; 358/111

[56] References Cited

PUBLICATIONS

Winick et al., "Synchrotron Radiation Research," Ann. Rev. Nucl. Part. Sci. 1978, 28:33-113.
Houk et al., "Real Time Digital K-Edge Subtraction Fluroscopy," Investigative Radiology, Jul.-Aug. 1979, vol. 14.

Primary Examiner—Kyle L. Howell
Assistant Examiner—Francis J. Jaworski
Attorney, Agent, or Firm—Flehr, Hohbach, Test, Albritton & Herbert

[57] ABSTRACT

Non-invasive angiography is provided through use of monochromatized synchrotron radiation in a dichromographic procedure. A small quantity of an iodinated compound is introduced into the blood stream of a patient. An X-ray picture of a blood vessel such as the coronary artery can be produced by directing synchrotron radiation from a storage ring source at first and second selected wavelengths or energy levels through the blood vessel, detecting the attenuated radiation to obtain first and second signals representative of the attenuated radiation, and logarithmically subtracting the two signals to essentially eliminate all background contrast. Due to the K-absorption edge of iodine the resulting signal will emphasize the blood vessel containing the iodine.

9 Claims, 2 Drawing Figures

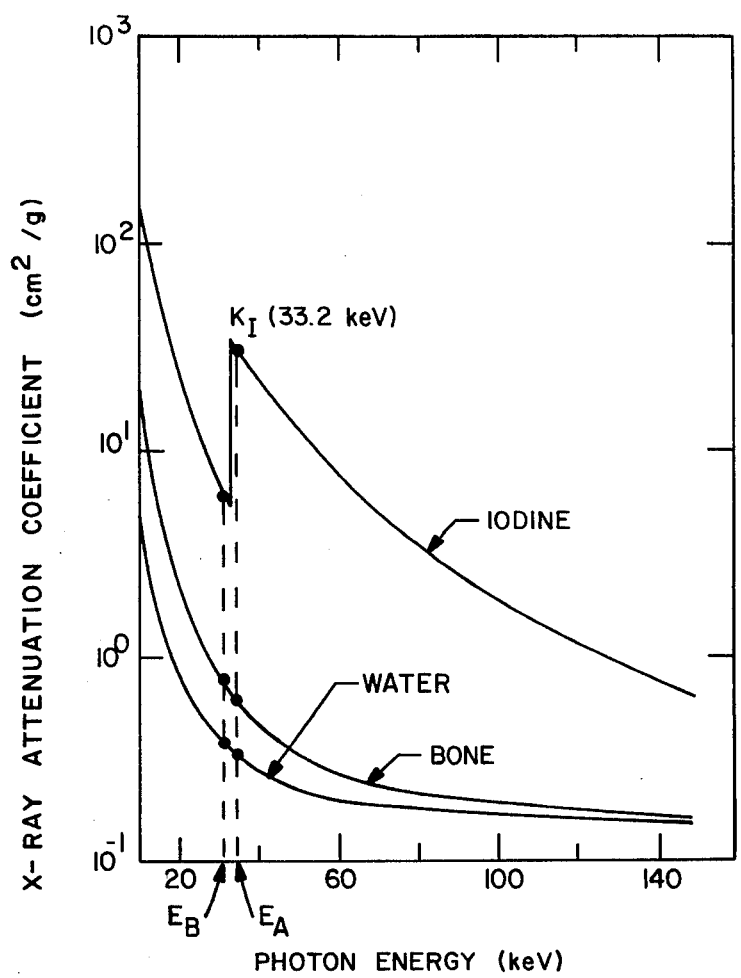
FIG.—1
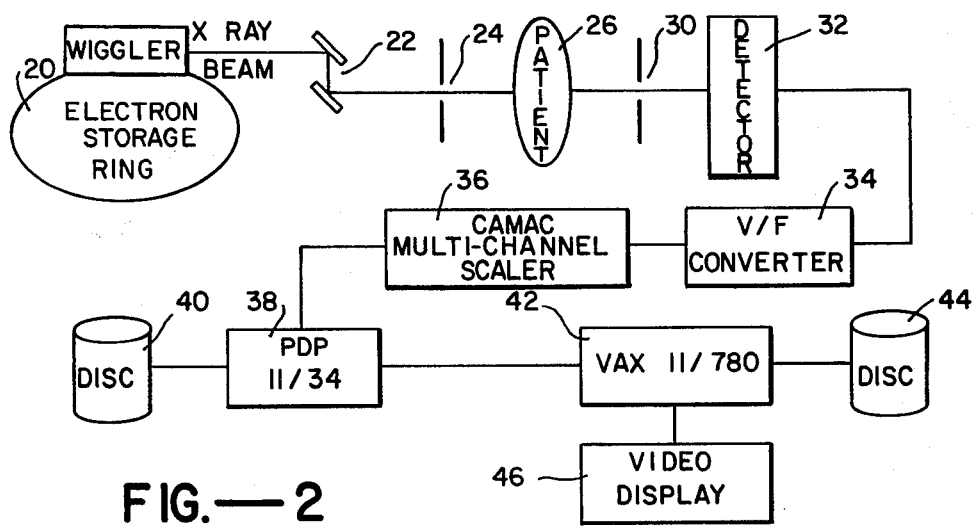
FIG.—2

METHOD AND MEANS FOR MINIMALLY INVASIVE ANGIOGRAPHY USING MONO-CHROMATIZED SYNCHROTRON RADIATION

This invention relates generally to a method and means for producing differential X-ray images using a contrast medium, and more particularly the invention relates to such a method and means for performing arteriorgraphy without requiring catherization of the artery to be imaged.

Because premature vascular disease is the major health problem in the United States today, it has become increasingly important to visualize abnormalities in the arteries of the heart, the neck, the brain and other vascular beds to detect the presence of dangerous obstructing lesions as well as the blood-flow patterns that develop in the vicinity of malignant tumors. Approximately 500,000 persons die each year from disease of the coronary arteries and many more suffer heart attacks and consequent heart damage. Approximately 50% of all deaths are cardiovascular in origin and one-fourth of all these patients are under 65 years of age. It is not surprising therefore that coronary artery examinations are increasing annually at a rate of about 20% and that 500,000 were performed last year in the United States alone. Many of these deaths and much of the disease could be prevented by surgery if a practical screening procedure existed.

Angiography, the radiologic visualization of blood vessels, containing contrast media, has become a powerful diagnostic tool that provides information not otherwise available. Because blood vessels absorb X-rays in a fashion similar to the surrounding soft tissues, they cannot be seen in routine examinations. Therefore, highly concentrated iodine-containing materials are injected directly into the arteries during the X-ray examination to provide the needed contrast.

The standard procedure for performing coronary arteriography requires catheterization of the artery in question and the injection, by this means, of a concentrated solution of an iodinated organic compound directly into the orifice of the artery in question immediately prior to the X-ray examination. This is a highly invasive and dangerous procedure associated with morbidity in one out of every 200 persons undergoing such a test. These risks are far too high to permit the use of angiography routinely to detect significant obstructions in the coronary arteries in the many persons known to be at risk. Furthermore, the cost of each such examination, which requires at least two days of hospitalization, exceeds $3,000 and the total national expenditure for this test now exceeds one billion dollars per year. Similar statistics could be cited in the instance of disease involving the arteries that supply the brain. There is an urgent need to reduce the risk and cost of these procedures.

One of the reasons for the dangerous invasive procedure now in use is that filtration of the X-rays that emanate from conventional sources, to exclude all frequencies except those maximally absorbed by iodine, leaves insufficient intensity of the beam to produce a useful picture in a time short enough to overcome arterial motion.

Dichromography is a known technique for obtaining differential X-ray images using a contrast medium such as iodine, barium, or xenon. Iodine, for example, has a K-absorption edge at 33.16 KeV whereby attenuation of X-rays slightly above 33.16 KeV is greater than the attenuation of X-rays slightly below 33.16 KeV. Therefore, by subtracting logarithmically radiograph signals at the two energy levels, suppression is effectively achieved for all unwanted information relating to absorption by soft tissue and bone. The image produced following the intravenous injection of iodine in an arm vein could produce a high fidelity picture of the entire circulatory tree. Although dichromography has been discussed in medical literature, its use for medical diagnostic purposes has met with limited success. Attempts at providing the necessary X-ray beams with requisite qualities have employed heavy filtration (90-95%) of beams of standard X-ray generators to obtain quasi-monochromatic beams of substantial line width and limited intensity. If only two quasi-monoenergetic beams are used, the method is limited essentially bone-free regions. If three quasi-monoenergetic beams are used, this restriction is removed. Each of the three quasi-monoenergetic beams, however, requires a different filter and at least one of the beams must have a different terminal voltage.

Accordingly, an object of the present invention is a safe, non-invasive method of visualizing blood vessels.

Another object of the invention is an improved method and apparatus for angiography using dichromographic techniques.

A feature of the invention is the use of monochromatized synchrotron radiation for producing differential X-ray images.

Briefly, in accordance with the invention, improved dichromographic angiography is realized by injecting an iodinated material into a vein such that the concentration of iodine in the blood stream is approximately 1-35 milligrams per milliliter. The patient is then exposed in quick succession to two monochromatic synchrotron X-ray beams, both immediately adjacent to the K-absorption edge of iodine but one with energy above and one with energy below the edge. This procedure is repeated in a vertical scan. The angiogram signals using the two X-ray beams are then detected, digitized, and mathematically processed thereby producing a difference signal which can be used to produce a contrast-enhanced image of the iodinated region.

In carrying out the method in accordance with the invention, intense X-ray beams with large horizontal width but with small vertical width at energies close to the K-absorption edge of iodine are provided from an electron storage ring. The X-rays are passed through a tunable X-ray monochromator to obtain precise energy values, and the X-rays are then used for scanning a patient. The signals derived from an X-ray detector are then scaled, digitized, and stored in a control computer which then generates an X-ray difference signal. Suitable display means is used for imaging the difference signal.

The invention and objects and features thereof will be more readily apparent from the following detailed description and appended claims when taken with the drawing, in which:

FIG. 1 is a plot of X-ray attenuation coefficient for different materials versus photon energy.

FIG. 2 is a functional block diagram of apparatus for producing differential X-ray images in accordance with the invention.

In reference to the drawing, FIG. 1 is a plot of X-ray attenuation coefficients versus photon energy for bone, water, and iodine. It will be noted that the attenuation coefficient continuously decreases for bone and water as a function of photon energy, but iodine exhibits an abrupt change in attenuation coefficient at an energy level of 33.16 KeV (the K-absorption edge). Other heavy elements such as barium and xenon also exhibit K-absorption edges at characteristic energies. Dichromography is based on obtaining radiographic signals using an X-ray energy slightly above the K-absorption edge and X-ray at an energy slightly below the K-absorption edge and then logarithmically subtracting the two signals to obtain a difference which is based essentially on the differences in attenuation at the K-absorption edge. Contrast due to bone, water, and tissue cancels out. A more detailed description of dichromography is given by Jacobson, ▷Dichromatic Absorption Radiography Dichromography" *Acta Radiologica*, Vol. 39, pgs. 437–452, June 1953; Mistretta et al, "Absorption Edge Fluoroscopy Using Quasi Monoenergetic X-Ray Beams", *Investigative Radiology*, Vol. 8, No. 6, pgs. 402–412, November-December 1973; Hauk et al, "Real Time Digital K Edge Subtraction Fluoroscopy", *Investigative Radiology*, Vol. 14, No. 4, pgs. 270–278, July-August 1979.

As above described, the effectiveness of dichromography for medical diagnostic purposes has been limited due to the necessity for using heavy filtration of X-ray beams to obtain quasi-monochromatic beams. In accordance with the present invention significantly improved dichromography is realized by using X-ray beams from an electron storage ring which is capable of producing monochromatic beams very close to the K edge of a heavy element such as iodine. The storage ring is a device for storing electrons in a closed orbit in a time varying magnetic field at nearly constant radius. These charged particles of low mass readily and continuously lose energy in the form of electromagnetic radiation when confined to the closed orbit. This radiation is called synchrotron radiation and, due to the extreme relativistic speed of the electrons, is emitted almost entirely in their orbit plane. In order to maintain the electrons in an orbit with constant energy, this radiated energy loss must be replaced promptly by powerful radiofrequency oscillators. At equilibrium the rate of production of synchrotron radiation by the orbiting electrons is equal to the amount of energy returned to them by the oscillator, both quantities being large. In effect, the electron storage ring is a device for the conversion of radiofrequency electromagnetic power into synchrotron radiation.

Despite the intensity of the synchrotron radiation emitted by electrons traversing simple dipole bending magnets, which are mandatory for storage ring operation, laboratories such as the Stanford Synchrotron Radiation Laboratory now rely upon special magnets, known as wiggler magnets, for the generation of their most powerful beams. These are described by Winick, H. and Spencer, J. E., "Wiggler Magnets at SSRL—Present Experience and Future Plans", *Nuclear Instruments and Methods*, Vol. 172, pgs. 45–53, 1980 and Spencer, J. E. and Winick, H., "Wiggler Systems as Sources of Electromagnetic Radiation", *Synchrotron Radiation Research*, Eds. H. Winick and S. Doniach, pgs. 663–713, Plenum Press, New York 1981. These magnets are irrelevant to the storage ring concept and are inserted into sections of the closed orbit where the electron beam curvature is usually zero. A wiggler magnet is designed with a periodic transverse magnetic field to enhance the emission of synchrotron radiation, but to transmit the electron beam with no net deflection.

FIG. 2 is a function block diagram of apparatus for developing differential X-ray images in accordance with the invention. Monochromatic radiation is obtained from the storage ring 20. The radiation emitted by the circulating electrons in the electron storage ring during a small angular fraction of their orbit is selected by horizontal aperture of angular width on the order of 6 mR. The radiation is conducted through a vacuum and then through a helium atmosphere to a double crystal silicon X-ray monochromator 22. The first crystal in the monochromator is oriented at an appropriate angle (e.g. 7°) to select, by Bragg diffraction, only a narrow band of X-ray wavelengths. The second crystal, which is in accurate alignment parallel with the first, serves to assure that the emergent X-ray beam exits from the monochromator in a direction parallel to the direction of the incident beam. In order to change the selected X-ray wavelength, or energy, it is necessary only to rotate simultaneously both crystals in the monochromator by the same small angle. In particular, in order to change the X-ray energy by the amount required to do iodine dichromography (e.g. 20 eV) the angle of rotation is only $3 \times 10^{-3\circ}$.

The radiation is then passed through an aperture 24 to the patient 26. At a distance of 25 meters from the orbiting electrons the selected X-ray beam has a horizontal profile that approximates a line. It is 15 cm in width and, if uncollimated, only 0.3 cm in height. However, the vertical width of the beam will be reduced to 0.5–1.0 mm by collimation of aperture 24. After this beam passes through the patient under examination, it passes through aperture 30 and is intercepted by a matching one-dimensional solid state X-ray detector 32. The multi-channel detector is segmented along its length and is able to record a one-dimensional projected image of the planar segment of the patient intercepted by the beam. Such detectors are known in the art, see for example U.S. Pat. No. 4,181,856. One embodiment of a solid state multi-channel detector 30 mm in width and 5 mm in height, fabricated to the applicants' specifications, incorporated 30 independent contiguous sensitive regions each 0.9 mm in width with a center-to-center spacing of 1.0 mm.

At each of the planar segments through the patient the image is recorded first at an X-ray energy just above the iodine K-edge and then, immediately following, at an energy just below the K-edge. A complete two-dimensional image of the body structure under examination is made by scanning either the beam or the patient vertically through the X-ray beam and recording pairs of one-dimensional images at each contiguous resolvable vertical position (~25–50 per inch). The image signal, at each energy and each vertical position, is passed through, for example, a voltage-to-frequency converter 34, and the frequency signal is then scaled by a Camac multi-channel scaler 36. The scaled signal is then passed to a computer 38 such as a PDP 11/34 and is recorded in digital form in a disc memory 40. A VAX 11/780 computer 42 and disc memory 44 control the display of the image signal on a video screen 46. At the discretion of the operator, the image may be manipulated on the screen or reprocessed in the computer to enhance any desired characteristic.

In order to visualize iodine within the coronary arteries it is necessary to record each pair of one-dimensional images, i.e. above and below the K-edge, in a time short compared to the periodic motion of these structures. An appropriate time interval is approximately 15 msec or less. The total time to scan the heart is longer than the cardiac cycle, but this relatively long scanning time will not result in a blurred image. Each line exposure, due to the high synchrotron X-ray intensity, will occupy only about 5 msec. The X-ray energy is then switched, within about 5 msec, and the second exposure is made. Each pair of line exposures occurs within 15 msec, a period within which the coronary arteries are essentially stationary. Upon completion of each exposure pair, either the beam or the patient is moved vertically by the required positional increment and the procedure repeated. The lack of blurring is governed by the line-pair exposure time and not by the total frame time.

The existing synchrotron X-ray beam at the Stanford Synchrotron Laboratory is capable of providing, after monochromatization, an X-ray intensity entirely adequate to record precise projected images even after transmission through thick body sections. Under standard operating conditions of the storage ring (e.g. a circulating electron current of 100 mA at an energy of 3 GeV) the existing wiggler-illuminated X-ray beam has an intensity of $6.8 \times 10^9$ photons/second/mm$^2$ of aperture at 20 meters from the storage ring. The bandwidth, at energies close to 33 KeV, is 15 eV. For comparison, a powerful modern X-ray generator of conventional design, dissipating 50 kilowatts of power, can provide $5 \times 10^9$ X-ray photons/second/mm$^2$ at 1 meter distance, but these photons are distributed over an energy range from 20–100 KeV. If this latter beam were to be monochromatized by the same method used with the synchrotron beam, its intensity would be reduced by a factor of approximately 2000.

After transmission through a tissue thickness of 20 cm the intensity of the synchrotron beam is $7.2 \times 10^6$ X-ray photon/second/image element of 1 mm$^2$, or $3.6 \times 10^4$ photons, in the required time exposure of 10 msec for coronary arteriography. The statistical noise contributed by this beam intensity to the X-ray image is only 1.1%, which can permit iodine concentrations as small as 1.1 mg/ml to be detected. This is much smaller than the concentration typically used in current clinical practice and, importantly, allows non-invasive angiography by means of venous injection of contrast agent.

While the invention has been described with reference to a specific embodiment, the description is illustrative of the invention and is not to be construed as limiting the invention.

One extension of the system could include the use of multiple X-ray beams simultaneously passing through the patient at different angles and corresponding multiple detectors. This would provide stereo imaging capability. It is also conceivable to rotate the patient through a single wide X-ray beam to record a tomographic image.

Various modifications and adaptions may occur to those skilled in the art without departing from the true spirit and scope of the invention. For example K-edge dichromography can be done with other contrast agents containing elements such as samarium or europium or others that provide contrast comparable with or better than iodine.

What is claimed is:

1. A method of visualizing arteries such as the coronary artery and other moving arteries comprising the steps of introducing a small quantity of an iodinated material into the blood stream of a patient, obtaining a first chromatized X-ray beam from an electron storage ring and auxiliary wiggler at an energy level slightly above 33.16 KeV, directing said first chromatized X-ray beam through the patient and the blood vessel under examination, obtaining a first signal indicative of said first chromatized X-ray beam as attenuated by said patient, obtaining a second chromatized X-ray beam from an electron storage ring and auxiliary wiggler at an energy level slightly below 33.16 KeV, directing said second chromatized X-ray beam through the patient and the blood vessel under examination, obtaining a second signal indicative of said second chromatized X-ray beam as attenuated by said patient, logarithmically subtracting said first signal from said second signal to obtain a third signal, and controlling a display with said third signal.

2. The non-invasive method as defined in claim 1 wherein said steps of obtaining a first chromatized X-ray beam and a second chromatized X-ray beam include passing radiation from an electron storage ring through a double-crystal silicon monochromator which is oriented at first and second positions with respect to said radiation.

3. The non-invasive method as defined by claim 1 wherein said step of introducing a small quantity of an iodinated compound establishes a concentration of iodine in the blood stream on the order of 1 to 35 mg/ml.

4. The non-invasive method as defined by claim 1, 2, or 3 wherein said first and second chromatized X-ray beams have an intensity on the order of $6.0 \times 10^9$ photons per second per square millimeter upon entry of the patient.

5. Apparatus for dichromographic angiography comprising an electron storage ring which produces x-rays, monochromator means including a double-crystal silicon monochromator, means for directing said x-rays from said storage ring to said monochromator means, collimating means for directing x-rays from said monochromator means to a patient, detector means for detecting attenuated radiation passing through the patient and generating an electrical signal indicative of the attenuated radiation, computer means for storing and operating on said electrical signal and generating a display control signal, and display means for displaying an image in response to said display control signal.

6. Apparatus for dichromographic angiography comprising an electron storage ring which produces x-rays, monochromator means, means for directing said x-rays from said storage ring to said monochromator means including a vacuum chamber and a helium filled chamber, collimating means for directing x-rays from said monochromator means to a patient, detector means for detecting attenuated radiation passing through the patient and generating an electrical signal indicative of the attenuated radiation, computer means for storing and operating on said electrical signal and generating a display control signal, and display means for displaying an image in response to said display control signal.

7. Apparatus as defined by claim 5 or 6 wherein said detector means includes a multichannel detector for generating a plurality of voltage signals in response to detected radiation, a voltage-to-frequency converter operably connected with said multichannel detector for converting said voltage signals to frequency signals, and scaling means operably connected to receive and scale said frequency signals.

8. Apparatus as defined by claim 5 or 6 wherein said detector means comprises a plurality of semiconductors.

9. Apparatus as defined by claim 5 or 6 wherein said detector means comprises a video image recorder.

* * * * *